United States Patent [19]

Gutman

[11] 4,124,637
[45] Nov. 7, 1978

[54] CERTAIN CYANODITHIOIMIDOCARBONATES

[75] Inventor: Arnold D. Gutman, Berkeley, Calif.

[73] Assignee: Stauffer Chemical Company, Westport, Conn.

[21] Appl. No.: 863,319

[22] Filed: Oct. 2, 1969

[51] Int. Cl.² .............................................. C07C 125/08
[52] U.S. Cl. .................................. 260/551 C; 424/320
[58] Field of Search ............................ 260/551, 551 C

[56] References Cited
U.S. PATENT DOCUMENTS 2,430,332  11/1947  Guy et al. ............................ 260/551
3,299,129  1/1967  D'Amico ............................. 260/551

OTHER PUBLICATIONS

Timmons et al., J. Org. CHem., vol. 32, pp. 1566-1572 (1967).

Primary Examiner—John D. Randolph
Attorney, Agent, or Firm—Edwin H. Baker

[57] ABSTRACT

Compounds of the formula

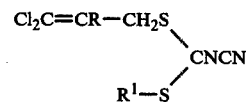

where R is hydrogen or chlorine and $R^1$ is methyl, allyl, dichlorobenzyl, or 1,1-dichloroallyl, and the use of the compounds to control bacteria, fungi or algae.

1 Claim, No Drawings

CERTAIN CYANODITHIOIMIDOCARBONATES

This invention relates to certain cyanodithioimidocarbonates and their use in controlling bacteria, fungi, and algae.

The compounds of this invention are those having the formula

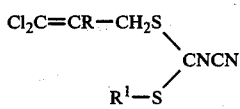

in which R is hydrogen or chlorine, and $R^1$ is methyl, allyl, dichlorobenzyl, or 1,1-dichloroallyl.

An article in the "*Journal of Organic Chemistry,*" The Chemistry of Cyanodithioimidocarbonic Acid, R. Jerome Timmons et al., Vol. 32, Pages 1,566–1,572, discloses a compound having the formula

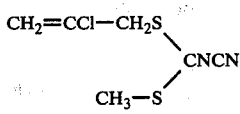

and one having the formula

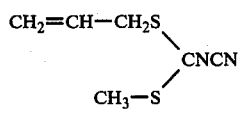

No utility is known to be disclosed for these two prior art compounds in the cited article or elsewhere in the prior art.

Applicant has found that the compounds of the present invention are unexplainably and unexpectedly superior to said prior art compounds in controlling such microorganisms as bacteria, fungi, and algae. More specifically, in certain comparative testing, as high as 10 fold superiority is realized with certain of the compounds of this invention compared to certain of the prior art compounds.

The compounds of the present invention can be prepared according to the following general reactions:

Step 1

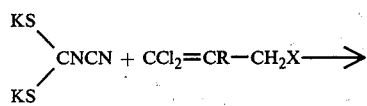

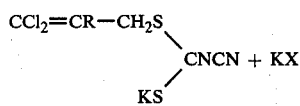

in which R is hydrogen or chlorine and X is chlorine, bromine, or iodine;

Step 2

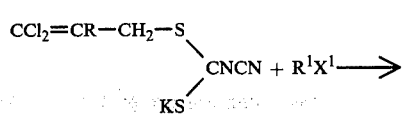

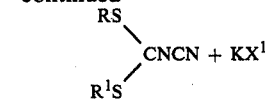

in which R is hydrogen or chlorine, and $R^1$ is methyl, allyl, $CCl_2\!=\!CH\!-\!CH_2$, or chlorobenzyl and $X^1$ is chlorine, bromine, or iodine.

In Step 1, about equal mole amounts of the reactants are used. A solution of the dipotassium cyanodithioimidocarbonate is formed in a mixture of about equal volume amounts of acetone and water, and to this at below 0° C., the halide reactant as an acetone solution is added dropwise with rapid stirring under a nitrogen atmosphere. After completion of the reaction, the reaction mixture is stirred for an additional 0.5 hour in an ice bath and for 3.5 hours at room temperature. The solution is dried and the product dried at 50° C. The dried product is purified by dissolving in acetone, filtration, evaporation of the solvent, washing the residue with ether twice.

In Step 2, the purified reaction product of Step 1 is combined with an equal mole amount of the halide reactant in acetone below 10° C. under a nitrogen atmosphere. The reaction mixture is refluxed for about an hour. The product is recovered and purified by conventional means such as by pouring the reaction mixture in benzene, washing the mixture 3 times with water, drying with anhydrous $MgSO_4$ followed by evaporation of the solvents under reduced pressure.

Preparation of the compounds of this invention is illustrated by the following Example:

EXAMPLE I 1,1,2-Trichloroallyl, allyl cyanodithioimido carbonate

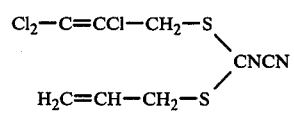

10gms. (0.051 moles) of potassium allylcyanodithioimidocarbonate and 9.2gms. (0.051 moles) of 1,1,2,3-Tetrachloropropene were combined in 200 ml. of acetone and heated under reflux for 1 hour. The resulting mixture was cooled and poured into 300 ml. of benzene. The benzene was washed with 3,100 ml. portions of water, dried with anhydrous $MgSO_4$, and evaporated under reduced pressure to yield 15.0 gms. (97.4% of theory) of 1,1,2-Trichloroallyl, allyl cyanodithioimidocarbonate. $N_D^{30} = 1.6104$ Other compounds of this invention preparable according to the aforesaid general and specific teaching are recited in the following Table.

TABLE I $Cl_2C\!=\!CR\!-\!CH_2\!-\!S\diagdown$
$\phantom{Cl_2C\!=\!CR\!-\!CH_2\!-\!S}CNCN$
$R^1\!-\!S\diagup$

| COMPOUND NUMBER | R  | $R^1$              | $N_D^{30}$ |
|-----------------|----|--------------------|------------|
| 1               | Cl | $CH_3$             | 1.6257     |
| 2               | Cl | $CH_2\!=\!CH\!-\!CH_2-$ | 1.6104 |
| 3               | H  | $CH_2\!=\!CH\!-\!CH_2-$ | 1.6067 |

TABLE I-continued $$Cl_2C=CR-CH_2-S\diagdown_{CNCN}$$
$$R^1-S\diagup$$

| COMPOUND NUMBER | R | $R^1$ | $N_D^{30}$ |
|---|---|---|---|
| 4 | H | ![Cl-substituted benzyl group: Cl\<benzene\>CH₂- with Cl] Cl-C₆H₃(Cl)-CH₂- | 1.6256 |
| 5 | H | $Cl_2C=CH-CH_2-$ | 1.5976 |

It has been found that the compounds of this invention are effective bacteriostatic and fungistatic agents, whereas microbiological growths on various substances cause deterioration by the presence of the infestation, the application of an agent to retard this adverse growth is desired. Such substances liable to fungus and bacterial infection include cloth, textiles, leather, paint, soaps, paper, wood, plastic, oil, cutting fluids, and the like. It is contemplated herein that the microbiocidal composition of the present invention may be effectively incorporated or applied to any of the substances susceptible to microbiological growths. The compound is also an effective paper mill slime control agent.

For maximum effectiveness, the active ingredients of the present invention are admixed in microbiostaticly effective amounts with an inert adjuvant. In order to provide formulations particularly adapted for ready and efficient application to the materials to be treated, such formulations comprise those of both the liquid and solid types, as well as the "aerosol" type formulations. Application can be directly to the substance to be protected from fungus or bacterial growth. In the pure state, the active ingredient may be too effective or too potent in some applications to have practical utility. A convenient method of treating cloth is by formulating the active ingredient with a soap or detergent and thereby imparting antiseptic or microbiocidal properties to the cloth as it is washed therewith.

For most effective protection, it is preferred to apply the materials in intimate contact, but thoroughly dispersed on or nearly in the surface to be protected. Therefore, the active ingredients have incorporated therewith a relatively inert agent or adjuvant as a dispersing medium, utilizing methods well-known to those skilled in the art.

More specifically, suitable formulations of the compounds of this invention comprise the above-defined active ingredients and a suitable material as an adjuvant therefore. Fungistat and bacteriostat compositions are advantageously formulated by first preparing a solution thereof in an organic solvent and then adding the resulting solution to water or to the carrier. If necessary, an emulsifying agent may be employed. The compositions may also be incorporated into solid carriers, such inert materials as clay, talc, pumice, and the like. It may also be incorporated in hand soaps, such as those containing sodium stearate, powdered soaps, or synthetic laundry detergent ingredients for control of bacteria and fungi which are washed with such materials. The chemical composition of these soaps and detergents is well-known to those skilled in the art. They may also be dissolved in liquefied gases such as fluorochloroethanes or methyl chloride and applied from aerosol bombs containing the solution. It should be noted that suitable formulations may also include adhesive agents, indicators, and other microbiocidal ingredients. Other ingredients may be supplementary insecticides, fungicides, bacteriocides, nematocides, or selective herbicides.

Since the amount of active agent of the present invention which is employed will vary with the microbiocidal effect sought, the utility of the treated material, type and dimensions of the material treated, it is evident that no rigid limits can be set forth on the quantity required. Determination of the optimum effective concentration for a specific performance is readily ascertainable by routine procedures, as will be apparent to those skilled in the art.

As previously mentioned, the herein described compounds are microbiostatic agents which are useful and valuable in controlling fungi and bacteria.

The compounds of this invention are tested as microbiocides in the following manner.

IN VITRO VIAL TESTS

The compounds are tested to determine the microbiostatic efficacy when in contact with growing fungi or bacteria in an artificial medium. For each candidate compound, four 1 ounce vials are partially filled, two with malt broth, and two with nutrient broth. The compound to be tested is placed in the vials at the desired concentration (expressed in parts per million). The vials containing malt broth are inoculated with water suspensions of spores of the desired fungi, *Aspergillus niger*, and *Penicillium italicum*, and cells of the bacteria, *Escherichia coli* and *Staphylococcus aureus*, are inoculated into the vials containing nutrient broth (one specie of organism per vial). The vials are then sealed and held for one week, after which time the growth of the organisms is observed and recorded. The tests are repeated using lower concentrations of the candidate compounds to determine the lowest concentration that can be used and still offer some control of the growth of the organism. Table I shows the results of the In Vitro tests.

TABLE I

| | In Vitro Test Lowest Effective Concentration (p.p.m.) | | | |
|---|---|---|---|---|
| | FUNGI | | BACTERIA | |
| Compound Number | Aspergillus niger | Penicillium italicum | Escherichia coli | Staphylococcus aureus |
| 1 | (1) | (1) | 10 | 5 |
| 2 | (0.5) | (0.5) | 50 | 5 |
| 3 | (5) | (1) | 50 | 10 |
| 4 | (5) | (5) | 50 | 5 |
| 5 | (5) | (1) | 50 | 10 |

( ) = Indicates partial control at this concentration

The compounds of this invention are tested for the control of algae by the following test.

ALGAECIDAL SCREENING TEST

Sufficient candidate compound is diluted in acetone to give a 0.5% solution which is then diluted into 20 milliliters of warm modified Jack Meyers Agar medium. The dilutions are such as to give concentrations of 1, 5, 10 and 50 μg./ml. of the test compound in 20 × 100 mm. Petri dishes. After the agar solidifies, Petri dishes are inoculated with organisms of *Scenedesmus obliquus* or *Chlorella pyrenoidosa* at the various levels. The samples are then allowed to grow at room temperature under fluorescent lamps using a 14 hour light period each day. After two weeks, the samples are examined for growth of Algae, and the lowest concentration for which at least some control is obtained is recorded as set forth in Table III.

TABLE III

| COMPOUND NUMBER | Lowest Effective Concentration (μg/ml.) | |
|---|---|---|
| | *SCENEDESMUS OBLIQUUS* | *CHLORELLA PYRENOIDOSA* |
| 1 | (5) | 10 |

( ) = Indicates partial control at this concentration

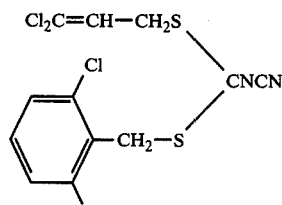

It is claimed:
1. The compound